United States Patent [19]

Morita et al.

[11] Patent Number: 4,769,480
[45] Date of Patent: Sep. 6, 1988

[54] BENZYLAMINE DERIVATIVE

[75] Inventors: Yoshiharu Morita, Yokohama; Naoshi Imaki, Atsugi; Hisao Takayanagi, Yokohama; Tadashi Shirasaka, Machida; Tetsuro Shimpuku, Yokohama; Yuki Takuma, Machida; Mari Oishi, Yokohama, all of Japan

[73] Assignee: Mitsubishi Chemical Industries Limited, Tokyo, Japan

[21] Appl. No.: 896,961

[22] Filed: Aug. 15, 1986

[30] Foreign Application Priority Data

Aug. 26, 1985 [JP] Japan .................................. 60-186963
Sep. 19, 1985 [JP] Japan .................................. 60-206795
Jan. 27, 1986 [JP] Japan .................................. 61-15366

[51] Int. Cl.$^4$ ........................................... C07D 317/64
[52] U.S. Cl. .................................................... 549/437
[58] Field of Search ......................... 549/437, 440, 443

[56] References Cited

U.S. PATENT DOCUMENTS 4,024,274 5/1977 Druckery et al. ................... 549/437

Primary Examiner—Nicky Chan
Assistant Examiner—Wendy B. Davis
Attorney, Agent, or Firm—Oblon, Fisher, Spivak, McClelland & Maier

[57] ABSTRACT

There is provided a novel benzylamine derivative of the formula I:

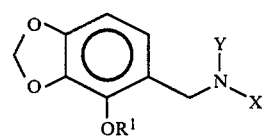

wherein $R^1$ represents a hydrogen atom or a methyl group, X represents a hydrogen atom, a methyl group or a tosyl group, and Y represents a hydrogen atom, a methyl group or

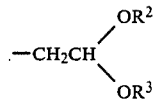

in which $R^2$ and $R^3$ being identical or different from each other represent independently a lower alkyl group.

10 Claims, No Drawings

BENZYLAMINE DERIVATIVE

The present invention relates to a novel benzylamine derivative which is useful for an intermediate in synthesis of Cotarnine, a main starting material for the production of Tritoqualine having a pharmacological activity of antiallergy. (Japanese Patent Application Laid-Open No. 59-44374 and No. 59-44382).

Cotarnine has been hitherto produced by oxidation of Noscapine which belongs to alkaloids (Yakugaku Zasshi, vol. 50, 559 (1930)).

However, Noscapine is obtained from natural products in a limited quantity, and its constant supply is therefore difficult.

According to the invention it has been found that a new benzylamine derivative of specific formula is effective as an intermediate for the production of Cotarnine and may advantageously be used in an industrial production of Cotarnine.

The present invention provides a new benzylamine derivative of formula I:

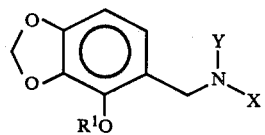 (I)

wherein $R^1$ represents a hydrogen atom or a methyl group, X represents a hydrogen atom, a methyl group or a tosyl group and Y represents a hydrogen atom, a methyl group or

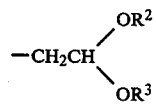

in which $R^2$ and $R^3$ being identical or different from each other represent independently a lower alkyl group, preferably of $C_1$-$C_5$ atoms, and more preferably $C_1$-$C_3$ atoms.

Examples of the compound of the formula I are shown below:
N-(2-methoxy-3,4-methylenedioxybenzyl-)aminoacetaldehyde dimethylacetal;
N-(2-methoxy-3,4-methylenedioxybenzyl-)aminoacetaldehyde diethylacetal;
N-(2-methoxy-3,4-methylenedioxybenzyl-)aminoacetaldehyde dipropylacetal;
N-(2-hydroxy-3,4-methylenedioxybenzyl-)aminoacetaldehyde dimethylacetal;
N-(2-hydroxy-3,4-methylenedioxybenzyl-)aminoacetaldehyde diethylacetal;
N-(2-hydroxy-3,4-methylenedioxybenzyl-)aminoacetaldehyde dipropylacetal;
N-(2-methoxy-3,4-methylenedioxybenzyl)-N-methylaminoacetaldehyde dimethylacetal;
N-(2-methoxy-3,4-methylenedioxybenzyl)-N-methylaminoacetaldehyde diethylacetal;
N-(2-methoxy-3,4-methylenedioxybenzyl)-N-methylaminoacetaldehyde dipropylacetal;
N-(2-hydroxy-3,4-methylenedioxybenzyl)-N-methylaminoacetaldehyde dimethylacetal;
N-(2-hydroxy-3,4-methylenedioxybenzyl)-N-methylaminoacetaldehyde diethylacetal;
N-(2-hydroxy-3,4-methylenedioxybenzyl)-N-methylaminoacetaldehyde dipropylacetal;
N-(2-methoxy-3,4-methylenedioxybenzyl)-N-(p-toluene-sulfonyl)aminoacetaldehyde dimethylacetal;
N-(2-methoxy-3,4-methylenedioxybenzyl)-N-(p-toluene-sulfonyl)aminoacetaldehyde diethylacetal;
N-(2-methoxy-3,4-methylenedioxybenzyl)-N-(p-toluene-sulfonyl)aminoacetaldehyde dipropylacetal;
N-(2-hydroxy-3,4-methylenedioxybenzyl)-N-(p-toluene-sulfonyl)aminoacetaldehyde dimethylacetal;
N-(2-hydroxy-3,4-methylenedioxybenzyl)-N-(p-toluene-sulfonyl)aminoacetaldehyde diethylacetal;
N-(2-hydroxy-3,4-methylenedioxybenzyl)-N-(p-toluene-sulfonyl)aminoacetaldehyde dipropylacetal;
2-methoxy-3,4-methylenedioxybenzylamine;
2-methoxy-3,4-methylenedioxybenzylamine hydrochloride;
2-hydroxy-3,4-methylenedioxybenzylamine;
2-hydroxy-3,4-methylenedioxybenzylamine hydrochloride;
N-(2-methoxy-3,4-methylenedioxybenzyl)-p-toluenesulfonamide;
N-(2-hydroxy-3,4-methylenedioxybenzyl)-p-toluenesulfonamide;
N-(2-methoxy-3,4-methylenedioxybenzyl)-N-methyl-p-toluene-sulfonamide;
N-(2-hydroxy-3,4-methylenedioxybenzyl)-N-methyl-p-toluene-sulfonamide;
N-methyl-2-methoxy-3,4-methylenedioxybenzylamine;
N-methyl-2-methoxy-3,4-methylenedioxybenzylamine hydrochloride;
N-methyl-2-hydroxy-3,4-methylenedioxybenzylamine;
N-methyl-2-hydroxy-3,4-methylenedioxybenzylamine hydrochloride.

The compound according to the present invention may occasionally be obtained in the form of salt such as hydrochloride and sulfate depending on the production process.

A process for production of the compound according to the invention will be described below.

The compound may be prepared by reacting a formyl compound of the formula VII:

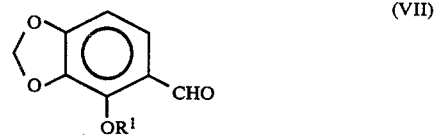 (VII)

wherein $R^1$ represents a hydrogen atom or a methyl group with an aminoacetal of the formula VIII:

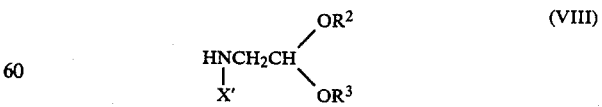 (VIII)

wherein X' represents a hydrogen atom or a methyl group and $R^2$ and $R^3$ being identical or different from each other represent independently a lower alkyl group, or with ammonia, methyl amine or hydroxylamine to obtain an imino compound and then reducing the imino group with a stoichiometrical reductant such as $NaBH_4$ and LiAlH$_4$ or catalytically reducing the same with hydrogen.

Examples of the aminoacetal of the formula VIII described above may include, for instance, aminoacetaldehydedimethylacetal, aminoacetaldehydediethylacetal, aminoacetaldehydedipropylacetal, N-methylaminoacetaldehydedimethylacetal, N-methylaminoacetaldehydediethylacetal and N-methylaminoacetaldehydedipropylacetal, which is preferably used in an excess over the formyl compound VII.

The formyl compound of the formula VII is a known compound and can be easily synthesized in a manner described in literatures published, for example, Chem. Ber., vol. 93, 360 (1960).

Ammonia, methylamine or hydroxylamine is preferably used in an excess over the formyl compound VII. The stoichiometrical reductant is preferably used in an excess over the formyl compound VII.

A catalyst used in the catalytic reduction may include, for example, PtO$_2$, Pt/C, Pt/alumina, Pd black, Pd/C and Pd/alumina, which is used in an amount of from 0.0001 to 10 mol % of the formyl compound VII. Hydrogen is used at normal or elevated pressure. Any solvent inactive to the reduction with the stiochiometrical reductant or the hydrogen may be used in each reaction. The reaction temperature is from 0° C. to 160° C. for both of the reduction methods.

The reduction may be carried out after completion of or together with the iminization.

After the reaction is over, the product may be obtained through the procedures of separation or hydrolysis of the catalyst, extraction of the reaction mixture and distillation of the solvent.

Alternatively, the compound according to the present invention may also be prepared by reacting a benzylamine compound of the formula I of which Y is a hydrogen atom with a haloacetal compound of the formula IV:

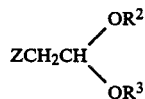

(IV)

wherein Z represents a halogen and R$^2$ and R$^3$ are as defined in the formula VIII.

Examples of the haloacetal compound IV may include, for instance, chloroacetaldehydedimethylacetal, chloroacetaldehydediethylacetal, chloroacetaldehydedipropylacetal, bromoacetaldehydedimethylacetal, bromoacetaldehydediethylacetal, bromoacetaldehydedipropylacetal, iodoacetaldehydedimethylacetal and iodoacetalodehydediethylacetal.

The haloacetal compound is used in an amount of from 0.5 to 10 moles, and preferably from 0.8 to 2.0 moles per mole of benzylamine compound. Any solvent may be used so long as it is inactive to the reaction.

Dehydrohalogenating agent, for example, tertiary amine such as triethylamine, pyridine and quinoline, or alkali such as sodium hydroxide and potassium hydroxide may be preferably used. They may be preferably used in an excess over haloacetal. The reaction temperature is from 0° C. to 150° C.

After the reaction is over, the product may be obtained through the procedures of hydrolysis or extraction of the catalyst and distillation of the solvent.

Further, the compound according to the present invention may also be prepared by a process of directly reacting a methylenedioxy compound of the formula IX:

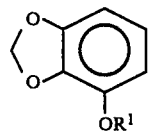

(IX)

wherein R$^1$ represents a hydrogen atom or a methyl group with formalin or paraformaldehyde and an aminoacetal of the formula VIII in which X' is a hydrogen atom.

Any solvent may be used so long as it is inactive to the reaction, and the reaction temperature is from ordinary temperature to 120° C. Formalin or paraformaldehyde is used in an amount of from 0.5 to 2.0 moles per mole of the methylenedioxy compound IX. Aminoacetal is used in an amount of from 0.5 to 2.0 moles per mole of the methylenedioxy compound IX.

After the reaction is over, the product with high purity may be obtained by distilling off the solvent, which may be further purified by means of column chromatography or recrystallization.

Furthermore, the compound of the formula I in which X is a methyl group may be prepared by reactinhg the compound I in which X is a hydrogen atom with an N-methylating agent such as formalin-NaBH$_4$, formalin-LiAlH$_4$, formalin-formic acid or formalin-hydrogen-(reducing)catalyst.

Any solvent may be used so long as it is inactive to the reaction, an alcohol solvent being preferable. The reaction temperature is from ordinary temperature to 120° C. and the reaction pressure is from atmospheric pressure to 100 kg/cm$^2$.

Formalin is preferably used in excess, and preferably in an amount of from 1.0 to 1.5 moles per mole of the starting compound I. NaBH$_4$, LiAlH$_4$ or formic acid may be a preferred reductant, and it is preferably used in an amount of from 1.0 to 1.5 moles per mole of the starting compound I. In the case of using hydrogen, the reaction may be carried out either at normal pressure or at elevated pressure. Any catalyst used in general catalytic reduction may be used in the catalytic reduction of the invention, and specifically, for example, PtO$_2$, Pt black, Pt/C, Pd black, Pd/C and Pd/alumina. It is used in an amount of from 0.0001 to 0.1 moles per mole of the starting compound I.

After the reaction is over, the product may be isolated by the hydrolysis in the case of using the stoichiometrical reductant or by the separation of the catalyst in the case of catalytic reduction and distillation of the solvent. The desired product thus obtained may be further purified by treating with an aqueous alkaline solution, extracting with CH$_2$Cl$_2$ and distilling off the solvent.

The above reaction may be carried out subsequently to the reaction between the formyl compound of the formula VII and methylamine, ammonia, hydroxylamine or aminoacetal.

Further, the compound of the formula I in which X is a tosyl group may be prepared by reacting the compound I in which X is a hydrogen atom with p-toluenesulfonyl halide. Any solvent may be used so long as it is inactive to the reaction, while hydrocarbon halide such as methylene chloride is preferable as the solvent. The reaction temperature is from 0° C. to 100° C. Dehydrohalogenating agent, for example, tertiary amine such as triethylamine, pyridine and quinoline may be preferable. The dehydrohalogenating agent may be preferably used in excess, and preferably in an amount of from 1.0 to 3 moles per mole of the starting compound I. While p-toluenesulfonyl halide includes chloride, bromide and iodide compounds, chloride is preferred among them. P-toluenesulfonyl halide may be preferably used in excess, and preferably in an amount of from 1.0 to 1.5 moles per mole of the starting compound I. The above reaction may be carried out subsequently to the reaction between the formyl compound of the formula VII and aminoacetal, methylamine, ammonia or hydroxylamine. After the reaction is over, the product may be obtained by hydrolysis, extraction of the reaction mixture and distillation of the solvent. Further, the product thus obtained may be isolated and purified through recrystallization from hydrocarbon solvent such as n-hexane.

Further, N-methylbenzylaminoacetal derivative of the formula II

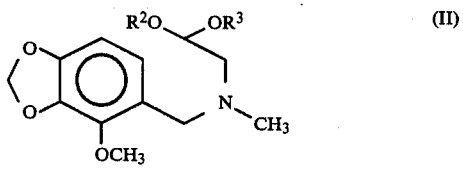

corresponding to the compound of the formula I in which $R^1$ represents a methyl group, X represents a methyl group and Y represents

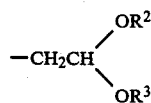

may be prepared by the following process. That is, N-methylbenzylaminoacetal derivative of the formula II described above may be prepared by reacting N-methyl-2-methoxy-3,4-methylenedioxybenzylamine of the following formula III:

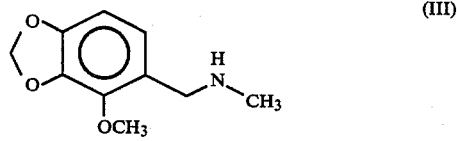

with a haloacetal compound of the following formula IV:

wherein $R^2$ and $R^3$ being identical or different from each other represent independently a lower alkyl group and Z represents a halogen, the reaction being carried out in the presence of an alkali and water.

N-methyl-2-methoxy-3,4-methylenedioxybenzylamine of the formula III, the starting material for the process, may be prepared by reacting 2-methoxy-3,4-methylenedioxybenzaldehyde with methylamine followed by hydrogenating the resultant product in the presence of the catalyst such as Pd/C.

Examples of the haloacetal compounds of the formula IV are as described above, which may be used in an amount of 0.5 to 10 moles, preferably, from 0.8 to 2 moles per mole of N-methyl-2-methoxy-3,4-methylenedioxybenzylamine.

The characteristics of this process is to carry out the reaction between N-methyl-2-methoxy-3,4-methylenedioxybenzylamine III and the haloacetal compound IV in the presence of the alkali and water.

The alkali herein mentioned includes, for example, hydroxide of alkali metal and alkaline earth metal such as sodium hydroxide, potassium hydroxide and calcium hydroxide; carbonate of alkali metal and alkaline earth metal such as sodium carbonate, potassium carbonate and calcium carbonate; and $C_1$-$C_4$ alkoxide of alkali metal such as sodium methoxide, potassium methoxide, sodium ethoxide, potassium ethoxide, sodium propoxide, potassium propoxide, sodium butoxide and potassium butoxide. Sodium hydroxide and potassium hydroxide are particularly preferred.

The alkali may be used in an amount of from 0.5 to 20 moles and preferably from 0.5 to 5 moles per mole of the haloacetal compound IV.

The presence of water is essential for dissolving the alkali, and water may be used in an amount of 0.1 to 1000 ml, and preferably from 0.5 to 100 ml per 1 g of N-methyl-2-methoxy-3,4-methylenedioxybenzylamine.

The reaction may proceed with or without solvent, and when using the solvent, any solvent inactive to the reaction may be optionally used. The reaction temperature is from 0° C. to 180° C., and preferably from 50° C. to 150° C.

After the reaction is over, the desired N-methylbenzylaminoacetal derivative II may be obtained by liquid separation or extraction of the reaction mixture and distillation of the solvent in accordance with the conventional manner. On the other hand, the reaction mixture may be used in the subsequent step without being subjected to the above isolation steps.

Furthermore, N-methylbenzylaminoacetal derivative of the foregoing formula II may be also prepared by the following process, that is, by reducing 1-methoxy-2,3-methylenedioxybenzaldehyde of the formula V:

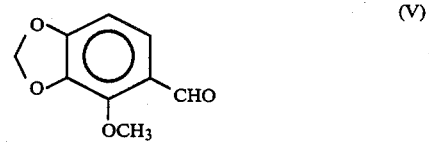

in the presence of an acetal of the formula VI:

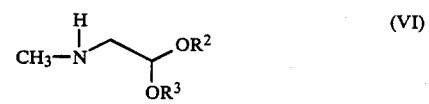

wherein $R^2$ and $R^3$ being identical or different from each other represent independently a lower alkyl group and an acid to produce the N-methyl-benzylaminoacetal derivative of the formula II:

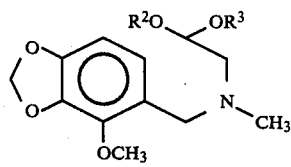

(II)

wherein $R^2$ and $R^3$ are as defined in the formula VI above.

The benzaldehyde derivative of the foregoing formula V is a known compound (Australian Journal of Chemistry, vol. 29, 2003, 1976).

The benzaldehyde derivative is synthesized by a known method (Organic Synthesis Collective vol. III, 759, Journal of The Chemical Society, Perkin Trans I, 1984, 709 and Australian Journal of Chemistry 29, 2003 (1976)) by starting from o-vanillin in accordance with the following reaction scheme.

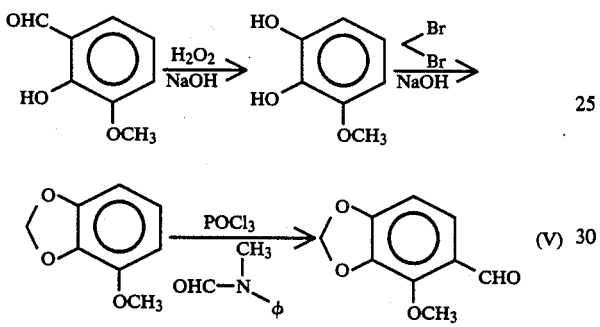

(V)

The acid in this process of the present invention may include, for example, organic or inorganic acid such as HCl, $H_2SO_4$, $CH_3COOH$, $CF_3COOH$ and p-toluene sulfonic acid, which is used in an amount of from 0.01 to 10 moles, and preferably from 0.1 to 2 moles per mole of the benzaldehyde.

$NaBH_3CN$ or $NaBH_4$ may be used as the reductant in this reduction process according to the present invention. But the catalytic hydrogenation in the presence of a solid catalyst, may show a better selectivity than $NaBH_3CN$ or $NaBH_4$.

By way of illustrating the solid catalyst, mention may be made of platinum group-based catalysts such as Pd/C, $Pd/Al_2O_3$ or $Pt/Al_2O_3$, Pt/C and $PtO_2$.

The reductant may be used in an amount of from 0.25 to 10 moles, and preferably from 1 to 2 moles per mole of the benzaldehyde, while the solid catalyst may be used in an amount of from 0.0001 to 0.01, and preferably 0.001 to 0.01 moles per mole of the benzaldehyde.

In this reaction, the hydrogen pressure is from 1 to 10 kg/cm²-G, and preferably from 1 to 2 kg/cm²-G.

Any solvent inactive to the reaction may be used as the reaction solvent. Alcohol solvent such as methanol and ethanol are preferably used. The reaction temperature is from 0° C. to 150° C., and preferably from 50° C. to 80° C.

The compound thus obtained is a useful intermediate for the production of Cotarnine.

The process for preparing Cotarnine from the compound of this invention may be illustrated, for example, in the following two routes.

The first route:

As shown by the following reaction scheme of the first route, N-methylbenzylaminoacetal (A) is cyclized in the presence of an acid into a tetrahydro-4-hydroxy-isoquinoline (B), which is then dehydroxylated in a reducing condition to obtain tetrahydroisoquinoline (C) followed by oxidation and hydrolysis thereof to prepare Cotarnine.

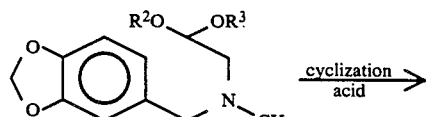

(A)

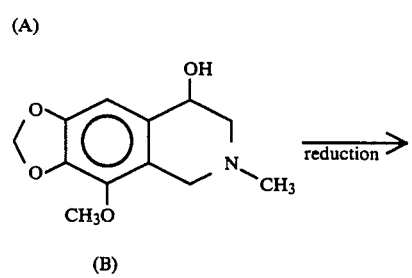

(B)

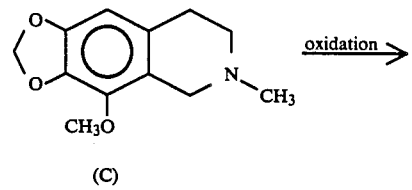

(C)

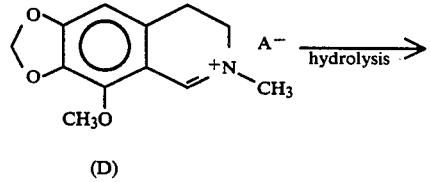

(D)

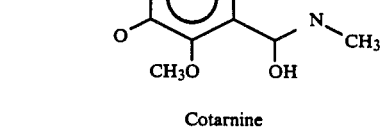

Cotarnine

In the above reaction scheme, $R^2$ and $R^3$ are as defined in the formula (I), and $A^-$ represents an anion.

In the first route, the reaction of (A)→(B) is carried out in the presence of the acid, which may include, for example, Brønsted acid such as sulfuric acid, hydrochloric acid, phosphoric acid and p-toluenesulfonic acid, as well as acidic ion exchange resins. The acid may be used in an optional amount, preferably in an excess over (A). Water is preferred as the solvent.

After the reaction is over, the compound (B) may be separated neutralizing the excessive acid with an alkali, alkalifying the reaction mixture, extracting it with an organic solvent such as methylene chloride, distilling off the solvent followed by recrystallizing the residue from an alcohol solvent such as ethanol.

The reaction of (B)→(C) is the reductive dehydroxylation, which is carried out by reacting $H_2$ with the compound (B) in the presence of the catalyst. The catalyst may be a usual catalyst for hydrogenation examples of which may include, for instance, PtO$_2$, Pt black, Pt/C, Pt/alumina, Pd black, Pd/C and Pd/alumina. H$_2$ may be used at either normal pressure or elevated pressure. Acidic Br∅nsted solvent, for example, acetic acid, sulfuric acid and hydrochloric acid may be preferred.

After the reaction is over, the compound (C) may be isolated by separation of the catalyst neutralization with an aqueous alkali, extraction of the reaction mixture and distillation of the solvent.

The reaction of (C)→(D)→Cotarnine is the oxidization of the compound (C) into the compound (D), which is then hydrolyzed into Cotarnine. Halogen-type oxidant, for example, I$_2$, Br$_2$, Cl$_2$, NaOCl, NaOBr, NaOI may be preferably used. Alcohol solvent is preferred.

In this reaction, the compound (D) may be once taken out and then converted into Cotarnine, or may be converted in situ into Cotarnine. Hydrolysis is carried out in an aqueous alkaline solution.

The Second Route:

There is also mentioned a process for synthesizing Cotarnine by another route represented by the following reaction scheme:

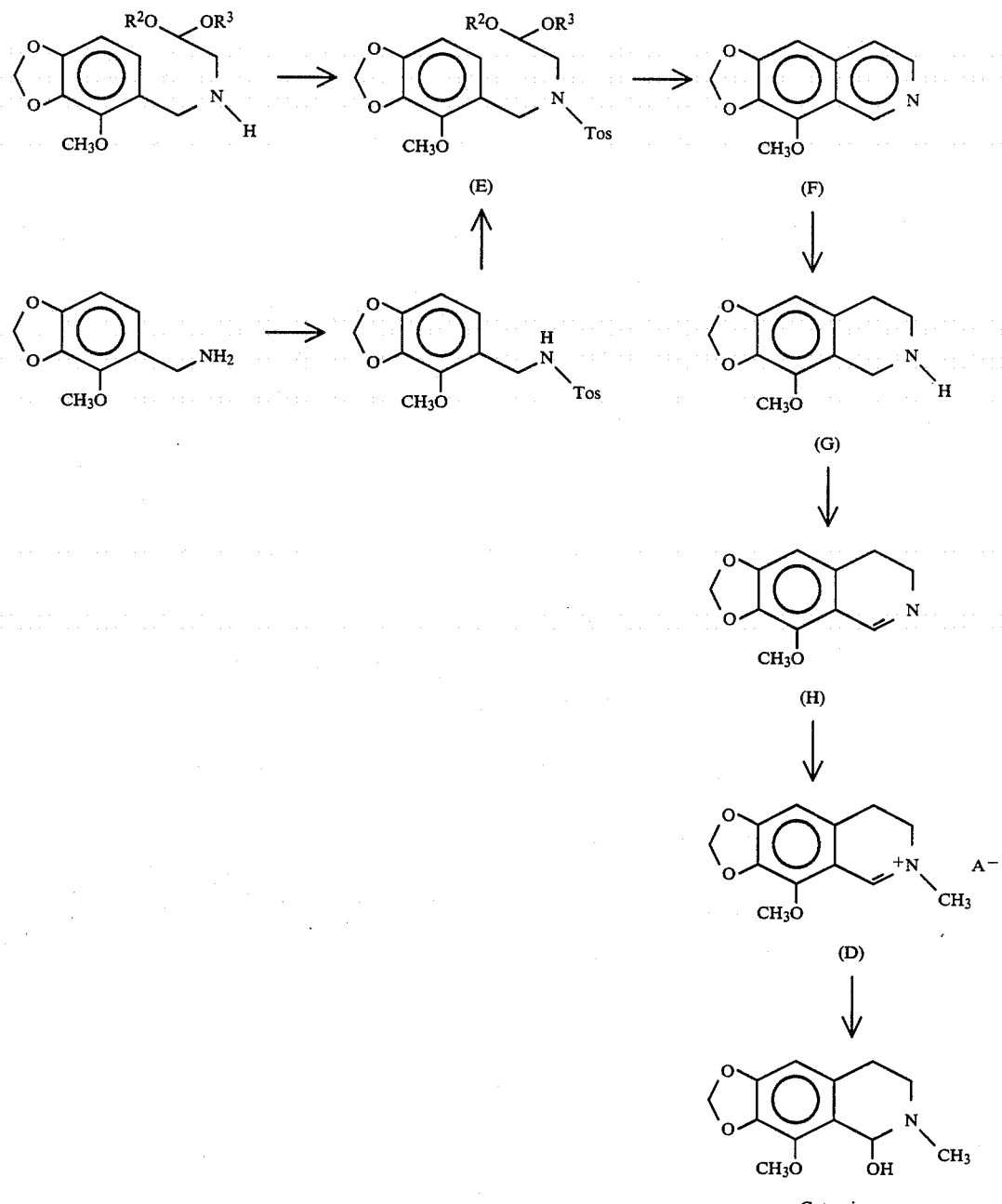

In the above reaction scheme, R$^2$ and R$^3$ are as defined in the formula (I), A$^-$ represents an anion and Tos represents a tosyl group.

The reaction of (E)→(F) is a cyclization in the presence of an acid, which may be carried out by the method described in a known literature (Journal of Chemical Society, Perkin Trans I, (1974), 2185).

The reaction of (F)→(G) is a reduction of an isoquinoline ring, which may be carried out by the method described in a known literature (Chem. Ber., 99, 267, 1966).

The reaction of (G)→(H) is an oxidizing and dehydrogenating reaction by the halogen-type oxidant such as NaOCl, NaOBr or NaOI. Alcohol and/or water may be preferably used as the solvent.

After the reaction is over, the compound (H) may be obtained by distilling off the solvent, extracting the residue with an organic solvent such as toluene and then distilling off the solvent.

The reaction of (H)→(D) is a methylation by dimethylsulfate, CH₃I or CH₃Br. The methylating agent may be preferably used in a slight excess over the compound (H). Any solvent may be used. The desired product is deposited out in the reaction solution, which may be then separated by filtration.

The reaction of (D)→Cotarnine is a hydrolysis, which may be carried out by the method described in a known literature (Ann. 395, 328, 1912).

This invention will now be described more specifically referring to examples, but these examples are not to be construed to limit the scope of the invention.

EXAMPLE 1

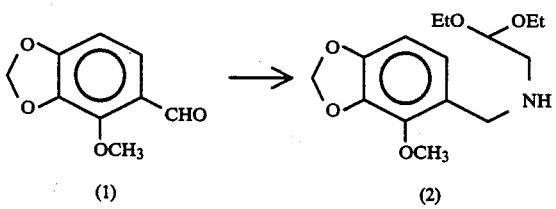

One gram of platinum oxide catalyst was added to 100 ml of ethanol, through which hydrogen was passed with stirring for 30 minutes. Then, 54.06 g (0.3 mol) of 2-methoxy-3,4-methylenedioxybenzaldehyde (1) and 40.78 g (0.3 mol) of aminoacetaldehyde diethylacetal (98 % purity) in 100 ml of ethanol were added to carry out hydrogenation with stirring at room temperature for 8.5 hours. The catalyst was filtered out and the solvent was distilled off under vacuum to obtain 89.43 g of N-(2-methoxy-3,4-methylenedioxybenzyl)aminoacetaldehyde diethylacetal (2) (yield 100 %) as an oil. IR and NMR spectra of the resultant product are listed below.

IR(neat, νmax cm⁻¹): 1630, 1495, 1465, 1255
¹H—NMR(60 MHz in CDCl₃, δppm):

| | | |
|---|---|---|
| 1.18 | (6H, t, J=7Hz, —OCH₂C$\underline{H}$₃ × 2) | |
| 1.88 | (1H, s, —N$\underline{H}$) | |
| 2.68 | (2H, d, J=6Hz, NC$\underline{H}$₂CH(OEt)₂) | |
| 3.3–3.9 | (4H, m, —OC$\underline{H}$₂CH₃ × 2) | |
| 3.70 | (2H, s, ArC$\underline{H}$₂N) | |
| 3.99 | (3H, s, OC$\underline{H}$₃) | |
| 4.58 | (1H, t, J=6Hz, NCH₂C$\underline{H}$(OEt)₂) | |

5.87    (2H, s, 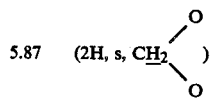 )

6.42    (1H, d, J=8Hz,<br>
6.70    (1H, d, J=8Hz, 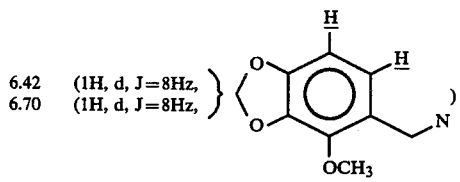 )

EXAMPLE 2

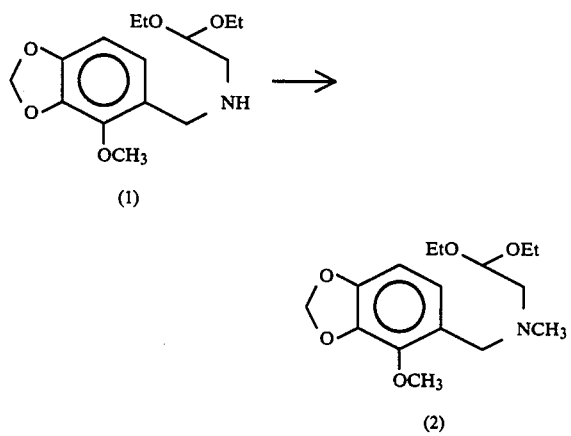

200 g of platinum oxide catalyst was added to a solution of 15 ml of ethanol and 2 ml of acetic acid, through which hydrogen was passed with stirring for 30 minutes. Then, 5.95 g (20 mmol) of N-(2-methoxy-3,4-methylenedioxybenzyl)aminoacetaldehyde diethylacetal (1) and 1.89 g (22 mmol) of 35% formalin were added to carry out hydrogenation with stirring at room temperature for one hour and 45 minutes. The catalyst was filtered out and the solution was concentrated under vacuum. 30 ml of methylene chloride and 15 ml of water were added to the residual oil and further 25% aqueous solution of sodium hydroxide was gradually added to make the aqueous layer basic. The resultant liquid is separated and the methylene chloride layer was washed with 15 ml of water and dried over anhydrous magnesium sulfate. Then, the resultant layer was filtered and concentrated under vacuum to obtain 61.5 g of N-(2-methoxy-3,4-methylenedioxybenzyl)-N-methylaminoacetaldehyde diethylacetal (2) (yield 99%) as an oil. IR and NMR spectra of the resultant product are listed IR(neat, νmax cm⁻¹): 1470, 1260, 1070
¹H—NMR(60 MHz in CDCl₃, δppm):

| | | |
|---|---|---|
| 1.19 | (6H, t, J=7Hz, OCH₂C$\underline{H}$₃ × 2) | |
| 2.26 | (3H, s, NC$\underline{H}$₃) | |
| 2.58 | (2H, d, J=5Hz, NC$\underline{H}$₂CH(OEt)₂) | |
| 3.3–3.9 | (4H, m, OC$\underline{H}$₂CH₃ × 2) | |
| 3.52 | (2H, s, ArC$\underline{H}$₂N) | |
| 3.96 | (3H, s, OC$\underline{H}$₃) | |
| 4.63 | (1H, t, J=5Hz, —NCH₂C$\underline{H}$(OEt)₂) | |

5.89    (2H, s, 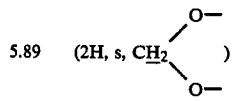 )

6.45    (1H, d, J=8Hz,<br>
6.80    (1H, d, J=8Hz, 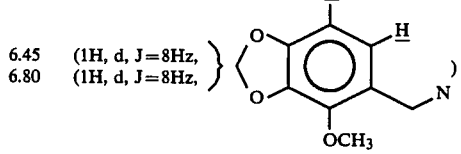 )

EXAMPLE 3

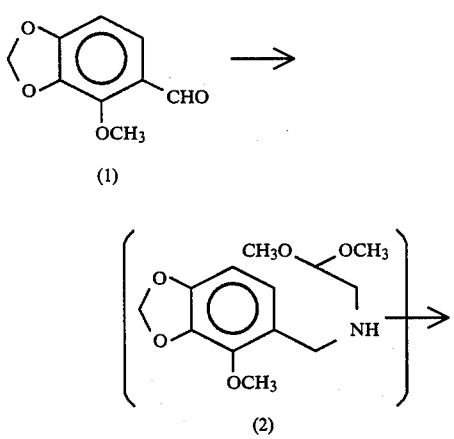

0.2 g of platinum oxide catalyst was added to 20 ml of methanol, through which hydrogen was passed to activate the catalyst. 10.81 g (60 mmol) of 2-methoxy-3,4-methylenedioxybenzaldehyde (1) and 6.37 g (60 mmol) of aminoacetaldehyde dimethylacetal (99% purity) in 20 ml of methanol were added to carry out hydrogenation for 3.5 hours. Then, 5.24 ml (66 mmol) of 35% formalin was added to carry out hydrogenation for 9 hours. The catalyst was filtered out and the filtrate was concentrated under vacuum to obtain 16.85 g of N-(2-methoxy-3,4-methylenedioxybenzyl)-N-methylaminoacetaldehyde dimethylacetal (3) as an oil (yield 99%). IR and NMR spectra of the resultant product are listed below.

IR(neat, $\nu$max cm$^{-1}$): 1475, 1265, 1070, 1050
$^1$H—NMR(60 MHz in CDCl$_3$, $\delta$ppm):

| | |
|---|---|
| 2.26 | (3H, s, NCH$_3$) |
| 2.55 | (2H, d, J=5Hz, NCH$_2$CH(OCH$_3$)$_2$) |
| 3.31 | (6H, s, CH$_2$CH(OCH$_3$)$_2$) |
| 3.49 | (2H, s, ArCH$_2$N) |
| 3.96 | (3H, s, ArOCH$_3$) |
| 4.51 | (1H, t, J=5Hz, NCH$_2$CH(OCH$_3$)$_2$) |
| 5.85 | (2H, s, CH$_2$<O—/O—) |
| 6.45 | (1H, d, J=8Hz,) |
| 6.78 | (1H, d, J=8Hz,) |

EXAMPLE 4

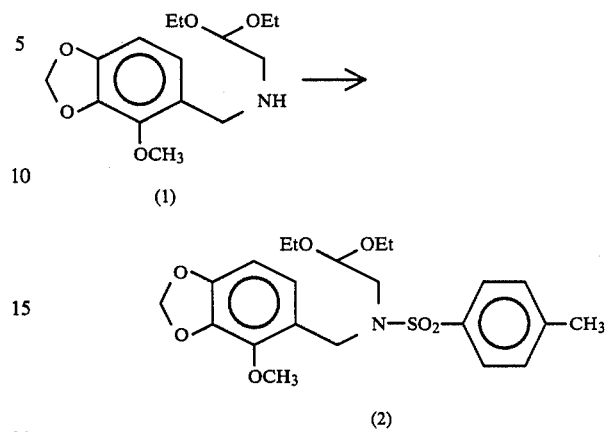

59.46 g (0.2 mol) of N-(2-methoxy-3,4-methylenedioxybenzyl)aminoacetaldehyde diethylacetal (1) and 28.45 ml (0.204 mol) of triethylamine were dissolved in 100 ml of methylene chloride, to which 38.8 g (0.204 mol) of p-toluenesulfonyl chloride in 80 ml of methylene chloride was added dropwise at 15°–30° C. for 25 minutes. After stirring at room temperature for 30 minutes, 150 ml of water was added to the reaction mixture, which was stirred followed by liquid separation and then being washed with 100 ml of water. After drying the methylene chloride layer over anhydrous magnesium sulfate, the solvent was distilled off under vacuum to obtain 90.3 g of N-(2-methoxy-3,4-methylenedioxybenzyl)-N-(p-toluenesulfonyl)aminoacetaldehyde diethylacetal (2) as an oil. Yield 100%. IR and NMR spectra of the resultant product are listed below.

IR(neat, $\nu$max cm$^{-1}$): 1470; 1340, 1265, 1160, 1070
$^1$H—NMR(60MHz in CDCl$_3$, $\delta$ppm):

| | |
|---|---|
| 1.13 | (6H, t, J=7Hz, OCH$_2$CH$_3$ × 2) |
| 2.40 | (3H, s, SO$_2$—C$_6$H$_4$—CH$_3$) |
| 3.2–3.8 | (6H, m, OCH$_2$CH$_3$ × 2 / NCH$_2$CH(OEt)$_2$) |
| 3.82 | (3H, s, —OCH$_3$) |
| 4.43 | (2H, s, ArCH$_2$N) |
| 4.58 | (1H, t, J=5Hz, NCH$_2$CH(OEt)$_2$) |
| 5.83 | (2H, s, CH$_2$<O—/O—) |
| 6.40 | (1H, d, J=8Hz,) |
| 6.77 | (1H, d, J=8Hz,) |

7.18 (2H, d, J=8Hz, 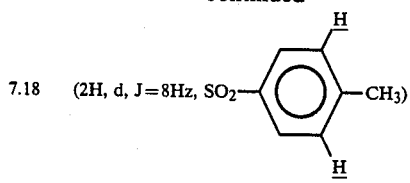

7.58 (2H, d, J=8Hz, 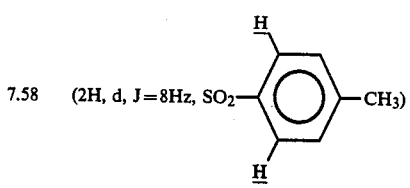

EXAMPLE 5

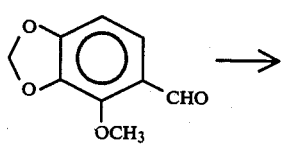

(1)

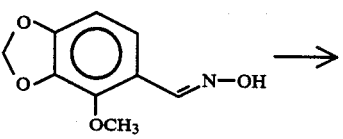

(2)

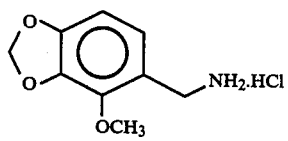

(3)

9.01 g (50 mmol) of 2-methoxy-3,4-methylenedioxybenzaldehyde (1) was dissolved in 40 ml of pyridine, to which 6.95 g (100 mmol) of hydroxylamine hydrochloride was added. The resulting mixture was heated to 100° C. for 45 minutes and then cooled. 300 ml of water was added and the reaction mixture was stirred for 30 minutes. The deposited crystals were filtered out, washed with water, and then dried under vacuum to obtain 9.27 g of 2-methoxy-3,4-methylenedioxybenzaldoxime (2). Yield 95%, m.p. 118°–9° C. IR and NMR spectra of the resultant product are listed below.

IR(KBr, νmax cm⁻¹): 3220, 1475, 1270, 1060, 950
¹H—NMR(60 MHz in CDCl₃, δppm):

4.00 (3H, s, OCH₃)

5.93 (2H, s, CH₂ 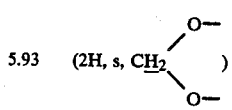 )

6.51 (1H, d, J=8Hz,<br>
7.17 (1H, d, J=8Hz, } 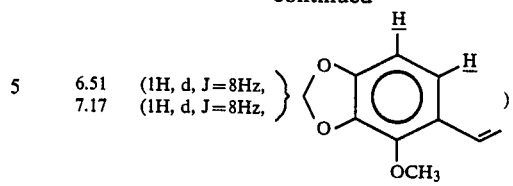 )

8.30 (1H, s, CH=NOH)
9.00 (1H, s, =NOH)

7.81 g (40 mmol) of 2-methoxy-3,4-methylenedioxybenzaldoxime (2) thus obtained, 3.67 ml (44 mmol) of concentrated hydrochloric acid and 500 mg of 5% palladium on carbon catalyst were added to 80 ml of ethanol to carry out hydrogenation at room temperature for 4 hours and 45 minutes. The catalyst was filtered out, the filtrate was concentrated and the residue is recrystallized from 60 ml of ethanol to obtain 4.86 g of 2-methoxy-3,4-methylenedioxybenzylamine hydrochloride (3). Yield 56%, m.p. 208°–210° C. IR and NMR spectra of the resultant product are listed below.

IR(KBr, νmax cm⁻¹): 2920, 1505, 1470, 1270, 1075
¹H—NMR(60 MHz in DMSO—d₆, δppm):

3.87 (2H, s, ArCH₂N)
4.00 (3H, s, OCH₃)

6.03 (2H, s, CH₂ 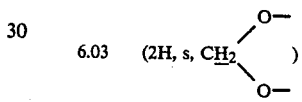 )

6.63 (1H, d, J=8Hz,<br>
7.00 (1H, d, J=8Hz, } 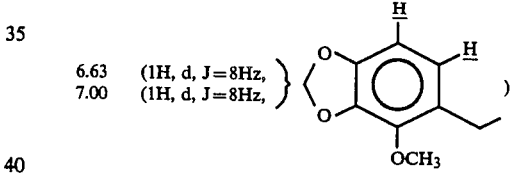 )

8.42 (3H, broad S, ArCH₂N⁺H₃)

EXAMPLE 6

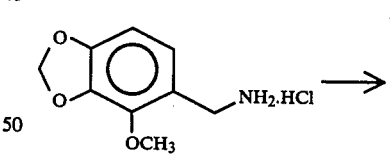

(1)

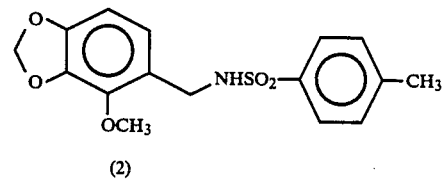

(2)

2.18 g (10 mmol) of 2-methoxy-3,4-methylenedioxybenzylamine hydrochloride (1) and 3.06 ml (22 mmol) of triethylamine were added to 30 ml of methylene chloride. Then, 1.91 g (10 mmol) of p-toluene sulfonyl chloride was added portionwise under water-cooling. The resulting mixture was stirred at room temperature for one hour. 20 ml of water was added for liquid separation. The methylene chloride layer was washed with 15 ml of water and dried over anhydrous magnesium sulfate followed by filtration thereof. The solvent was distilled off under vacuum. 30 ml of n-hexane was added to the residue and stirred for 30 minutes. The resulting crystals were collected by filtration, washed with n-hexane and dried to obtain 3.25 g of N-(2-methoxy-3,4-methylenedioxybenzyl)-p-toluenesulfonic amide (2) (yield 97%). It was recrystallized from ethyl acetate, m.p. 150°–151° C. IR and NMR spectra of the resultant product are listed below.

IR(KBr, νmax cm⁻¹): 3180, 1470, 1265, 1165, 1080, 1050
¹H—NMR(60 MHz in CDCl₃, δppm):

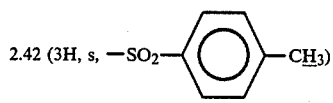
2.42 (3H, s, —SO₂—⌬—CH₃)

3.91 (3H, s, OCH₃)

4.05 (2H, d, J=6Hz, ArCH₂NH)

5.00 (1H, t, J=6Hz, ArCH₂NH)

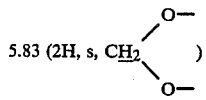
5.83 (2H, s, CH₂⟨O—/O—⟩)

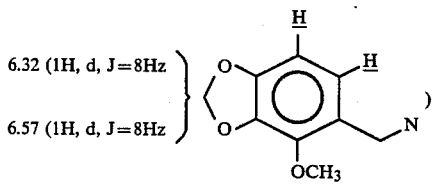
6.32 (1H, d, J=8Hz)
6.57 (1H, d, J=8Hz)

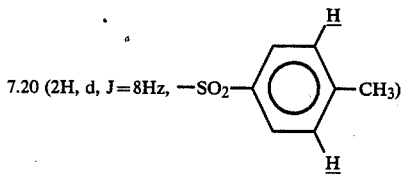
7.20 (2H, d, J=8Hz, —SO₂—⌬—CH₃)

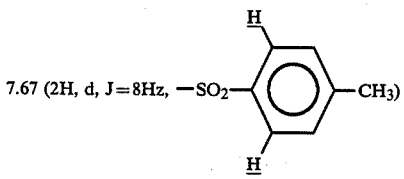
7.67 (2H, d, J=8Hz, —SO₂—⌬—CH₃)

EXAMPLE 7

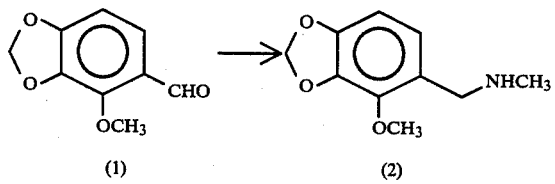

0.2 g of platinum oxide catalyst was added to 10 ml of ethanol, through which hydrogen was passed with stirring for 30 minutes. 5.41 g (30 mmol) of 2-methoxy-3,4-methylenedioxybenzaldehyde and 2.56 g (33 mmol) of 40% aqueous methylamine solution in 15 ml of ethanol were added to carry out catalytic reduction for 3 hours. Then, the catalyst was filtered out and the filtrate was concentrated under vacuum to obtain 5.82 g of N-methyl-2-methoxy-3,4-methylenedioxybenzylamine (2) as an oil (yield 99%). IR and NMR spectra of the resultant product are listed below.

IR(neat, νmax cm⁻¹): 1630, 1470, 1260, 1070, 1045
¹H—NMR(60 MHz in CDCl₃, δppm):

1.44 (1H, s, NH)

2.37 (3H, s, NCH₃)

3.63 (2H, s, ArCH₂N)

3.98 (3H, s, —OCH₃)

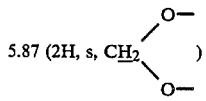
5.87 (2H, s, CH₂⟨O—/O—⟩)

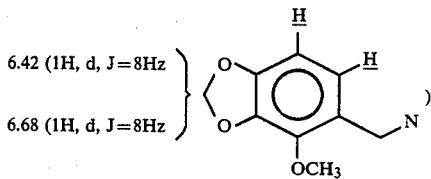
6.42 (1H, d, J=8Hz)
6.68 (1H, d, J=8Hz)

REFERENCE EXAMPLE 1

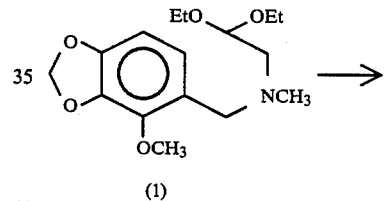
(1)

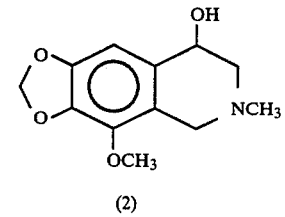
(2)

62.29 g (0.2 mol) of N-(2-methoxy-3,4-methylenedioxybenzyl)-N-methylaminoacetaldehyde dimethylacetal (1) obtained in Example 2 was dissolved in 400 ml of 6N sulfuric acid. After stirring at 76°–78° C. for 1.5 hours, the reaction mixture was cooled and pH was adjusted to about 11 by adding 25% aqueous solution of sodium hydroxide at temperature lower than 30° C. It was extracted with 200 ml and then 100 ml of methylene chloride successively, which were combined and washed with 100 ml of water and then dried over anhydrous magnesium sulfate. The salt was filtered out and the filtrate was concentrated under vacuum. The residue was dissolved under heating by adding 120 ml of ethanol and then cooled to 5° C. to deposit crystals. The crystals were collected by filtration, washed with 30 ml of cold ethanol and then dried under vacuum to obtain 38.09 g (yield 83%) of 4-hydroxy-8-methoxy-2-methyl-6,7-methylenedioxy-1,2,3,4-tetrahydroisoquinoline (2), m.p. 152°-3° C. IR and NMR spectra of the resultant product are listed below.

IR(KBr, νmax cm⁻¹): 1480, 1460, 1265, 1095, 1045
¹H—NMR(60 MHz in CDCl₃, δppm):

2.38 (3H, s, NCH₃)

2.40 (1H, dd, J=12Hz, 3Hz)

2.85 (1H, dd, J=12Hz, 3Hz)

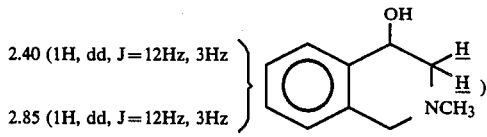

2.92 (1H, d, J=16Hz)

3.57 (1H, d, J=16Hz)

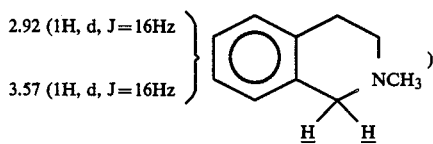

3.97 (3H, s, OCH₃)

4.42 (1H, broad S,

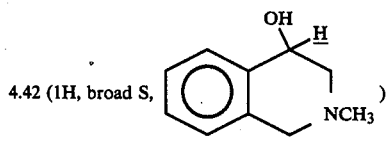 )

5.85 (2H, s, CH₂ 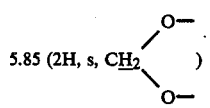 )

6.56 (1H, s, 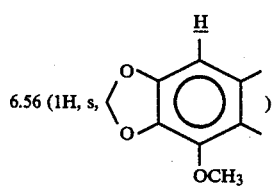 )

REFERENCE EXAMPLE 2

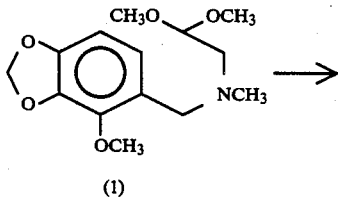
(1)

5.67 g (20 mmol) of N-(2-methoxy-3,4-methylenedioxybenzyl)-N-methylaminoacetaldehyde dimethylacetal (1) obtained in Example 3 was dissolved in 40 ml of 6N sulfuric acid. After stirring at 76°-7° C. for 1.5 hours, the reaction mixture was cooled and the pH was controlled to about 11 by adding 25% aqueous solution of sodium hydroxide at a temperature lower than 30° C. It was extracted with 35 ml and then 10 ml of methylene chloride successively, which were combined and washed with 20 ml of water and then dried over anhydrous magnesium sulfate. The solvent was concentrated under vacuum, the residue was dissolved under heating by adding 12 ml of ethanol and then cooled to 5° C. to deposit crystals. The crystals were collected by filtration, washed with 3 ml of cold ethanol and then dried under vacuum to obtain 3.71 g (yield 78%) of 4-hydroxy-8-methoxy-2-methyl-6,7-methylenedioxy-1,2,3,4-tetrahydroisoquinoline (2), m.p. 152°-3° C.

REFERENCE EXAMPLE 3

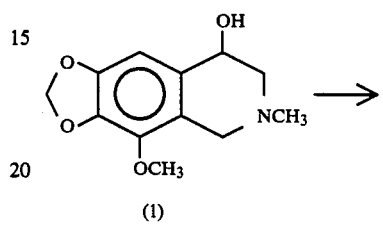
(1)

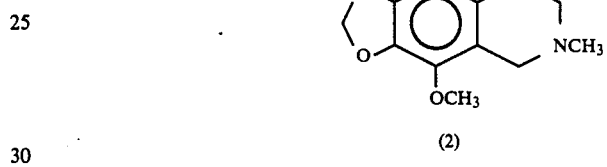
(2)

1.19 g (5 mmol) of 4-hydroxy-8-methoxy-2-methyl-6,7-methylenedioxy-1,2,3,4-tetrahydroisoquinoline (1) obtained in Reference Example 1 or 2 was dissolved in 15 ml of acetic acid, to which 0.33 ml (6 mmol) of 97% sulfuric acid and 500 mg of 5% palladium on carbon catalyst were added to carry out catalytic reduction at 75° C. for 2 hours. The catalyst was filtered out and 2 ml of 25% aqueous sodium hydroxide solution and 5 ml of water were added to the reaction mixture, which was concentrated under vacuum. 10 ml of water was added to the residue, the solution was made basic with 25% aqueous sodium hydroxide solution and extracted with 10 ml and then 5 ml of methylene chloride successively. The liquid extract was washed with 5 ml of water, dried over anhydrous magnesium sulfate and then concentrated under vacuum to obtain 1.03 g of 8-methoxy-2-methyl-6,7-methylenedioxy-1,2,3,4-tetrahydroisoquinoline. Yield 93%.

REFERENCE EXAMPLE 4

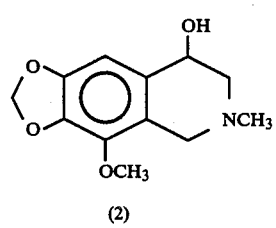
(2)

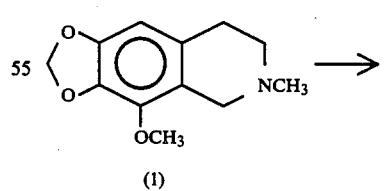
(1)

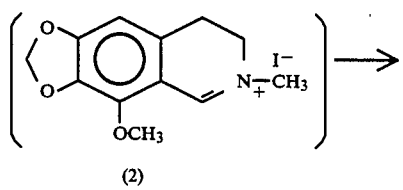
(2)

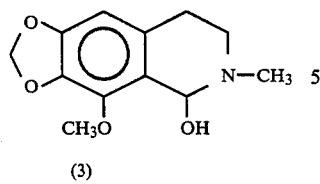

(3)

221 mg (1 mmol) of 8-methoxy-2-methyl-6,7-methylenedioxy-1,2,3,4-tetrahydroisoquinoline (1) obtained in Reference Example 3 and 108 mg (1.1 mmol) of potassium acetate were dissolved in 2 ml of ethanol, to which 254 mg (1 mmol) of iodine in 2.4 ml of ethanol solution was added dropwise for 85 minutes while heating at about 75° C. After heating at 75° C. for 100 minutes, ethanol was distilled off under vacuum and 6 ml of water was added to the residue. The resulting solution was cooled with ice and incorporated with 0.6 ml of 25% aqueous solution of sodium hydroxide. After stirring at room temperature for 30 minutes, crystals were collected by filtration, washed with each 0.6 ml of water twice and then dried to obtain 217 mg of cotarnine (3). Yield 91%.

EXAMPLE 8

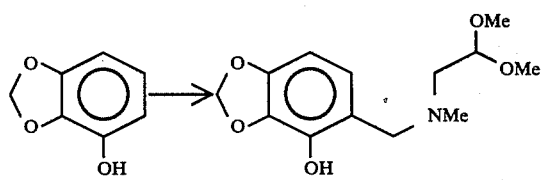

(1)  (2)

0.51 ml (4 mmol) of methylaminoacetaldehyde dimethylacetal (98% purity) and 150 mg (5 mmol) of paraformaldehyde were added to 690 mg (5 mmol) of 2,3-methylenedioxyphenol (1) in 5 ml of toluene. The resulting mixture was kept in a bath at 90° C. while stirring for 30 minutes. After distilling off toluene, the residue was separated and purified by silica gel column chromatography (developer:n-hexane/ethyl acetate=2/1) to obtain 890 mg (yield 80%) of N-(2-hydroxy-3,4-methylenedioxybenzyl)-N-methylaminoacetaldehyde dimethylacetal (2). IR and NMR spectra of the resultant product are listed below.

IR(neat, $\nu$max cm$^{-1}$): 1645, 1485, 1370, 1060
$^1$H—NMR(60 MHz in CDCl$_3$, $\delta$ppm):

2.27 (3H, s, NC$\underline{H}_3$)

2.61 (2H, d, J=5.5Hz, NC$\underline{H}_2$CH(OMe)$_2$)

3.30 (6H, s, OC$\underline{H}_3$ × 2)

3.60 (2H, s, 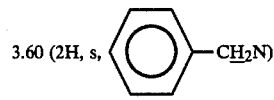—C$\underline{H}_2$N)

5.80 (2H, s, C$\underline{H}_2$⟨O—/O—⟩)

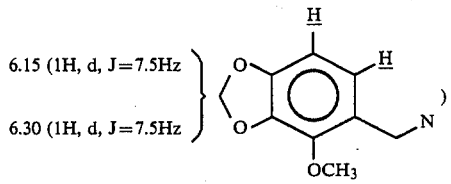

6.15 (1H, d, J=7.5Hz)
6.30 (1H, d, J=7.5Hz)

EXAMPLE 9

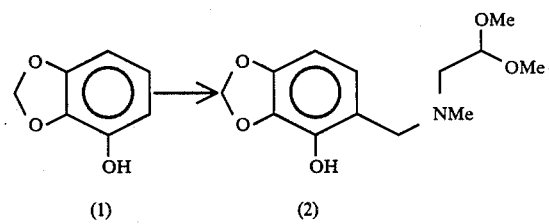

(1)  (2)

1.93 ml (15 mmol) of methylaminoacetaldehyde dimethylacetal (98% purity) was added to 1.38 g (10 mmol) of 2,3-methylenedioxyphenol (1) and 1.71 g (15 mmol) of 35% formalin solution in 12.5 ml of ethanol. The resulting mixture was heated under reflux for 5 hours. After distilling off ethanol, the residue was separated and purified by silica gel column chromatography (developer:n-hexane/ethyl acetate=1) to obtain 1.21 g (yield 47%) of the desired N-(2-hydroxy-3,4-methylenedioxybenzyl)-N-methylaminoacetaldehyde dimethylacetal (2).

EXAMPLE 10

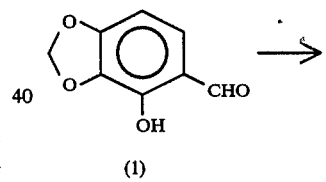

(1)

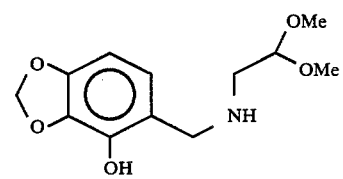

(2)

4.08 g of 2-hydroxy-3,4-methylenedioxybenzaldehyde (1) was added to 2.60 g of aminoacetaldehyde dimethylacetal (99% purity) in 300 ml of toluene. After heating under reflux for one hour, toluene was distilled off. The residue was dissolved in 300 ml of methanol, to which 313 mg of sodium borohydride was added while being stirred in an ice bath. After the reaction was over, methanol was distilled off, and water and ethanol were added to the residue. After the aqueous layer was made once acidic, it was neutralized with an aqueous solution of sodium hydrogen carbonate. The ether layer was separated, washed with water, dried over MgSO$_4$ and then concentrated to obtain 5.26 g (yield 78.4%) of N-(2-hydroxy-3,4-methylenedioxybenzyl)aminoacetaldehyde dimethylacetal (2) as an oil. IR and NMR spectra of the resultant product are listed below.

IR(neat, νmax cm⁻¹): 3320, 1645, 1480, 1365, 1060
¹H—NMR(60 MHz in CDCl₃, δppm):

2.77 (2H, d, J=5.5Hz, NCH₂CH(OMe)₂)

3.36 (6H, s, OCH₃ × 2)

3.96 (2H, s, 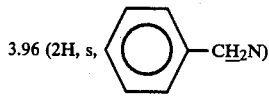)

4.46 (1H, t, J=5.5Hz, CH(OMe)₂)

5.93 (2H, s, 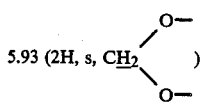)

6.29 (1H, d, J=8.0Hz)
6.46 (1H, d, J=8.0Hz) 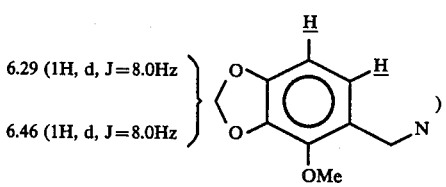

EXAMPLE 11

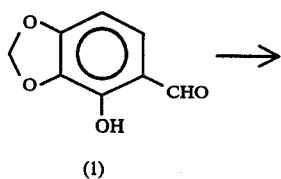
(1)

→

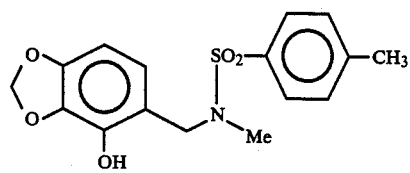
(2)

6.7 g of 2-hydroxy-3,4-methylenedioxybenzaldehyde (1) was dissolved in 300 ml of methanol, to which 10 ml of 40% aqueous solution of methylamine was added. After heating under reflux for 30 minutes, the reaction mixture was cooled in an ice-water bath and 510 mg of sodium borohydride was added with stirring. Methanol was distilled off and the obtained residue was dissolved in water. After the solution was once acidified, it was readily neutralized with an aqueous solution of sodium hydrogen carbonate. Organic layer was extracted with ether, the ether layer was washed with water, dried over MgSO₄ and concentrated. 3.57 g of the residue was dissolved in 30 ml of dry pyridine, to which 7.52 g of p-toluene sulfonic chloride was added. The resulting mixture was reacted at a room temperature for 3 hours. The reaction mixture was poured into ice water and extracted with ether. The ether layer was washed with water, dried over MgSO₄ and concentrated. 80 ml of 1N aqueous solution of sodium hydroxide and 80 ml of methanol were added to the 7.13 of the obtained residue and heated under reflux for 5 hours. On cooling to a room temperature, methanol was distilled off. After the solution was acidified, it was extracted with ether. The ether layer was washed with water, dried over MgSO₄ and then concentrated to obtain 4.40 g (yield 31.0%) of N-(2-hydroxy-3,4-methylenedioxybenzyl)-N-methyl-p-toluene sulfonamide as crystals (recrystallizing solvent: ether), m.p. 125°-6° C. IR and NMR spectra of the resultant product are listed below.

IR(KBr disk, νmax cm⁻¹): 3470, 1490, 1330, 1160, 1060
¹H—NMR(90 MHz in CDCl₃, δppm):

2.44 (3H, s, SO₂—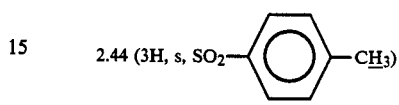—CH₃)

2.67 (3H, s, NCH₃)

4.03 (2H, s, CH₂NCH₃)

5.95 (2H, s, —OCH₂O—)

6.35 (1H, d, J=5.5Hz)
6.50 (1H, d, J=5.5Hz) 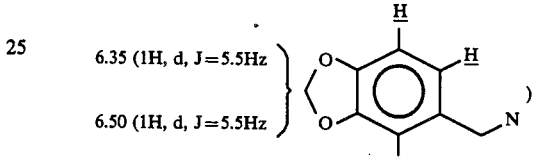

7.37 (2H, d, J=5.5Hz, SO₂—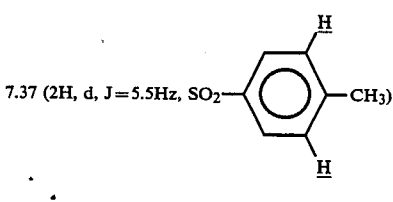—CH₃)

7.70 (2H, d, J=5.5Hz, SO₂—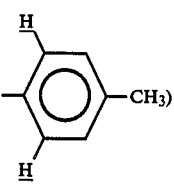—CH₃)

EXAMPLE 12

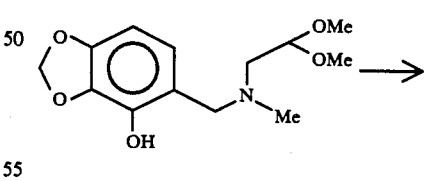
(1)

→

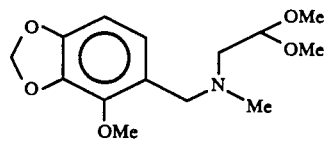
(2)

432 mg of N-(2-hydroxy-3,4-methylenedioxybenzyl)-N-methylaminoacetaldehyde dimethylacetal (1) was dissolved in 1 ml of ethyl ether, to which 3 ml of ethyl ether containing an excessive diazomethane was added. The resulting mixture was stirred at room temperature overnight. Ether was distilled off to obtain 455 mg of N-(2-methoxy-3,4-methylenedioxybenzyl)-N-methylaminoacetaldehyde dimethylacetal (2) (yield: quantitative).

EXAMPLE 13

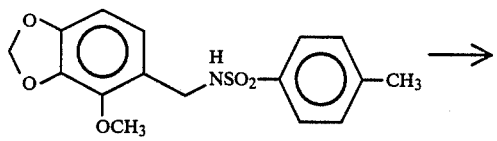

(1)

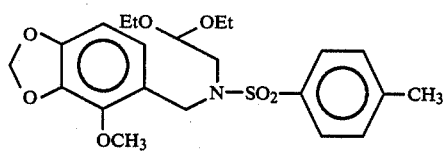

(2)

44 mg (1.1 mmol) of 60% oil dispersion of sodium hydride was washed twice with 2 ml of dry hexane to eliminate oil. 2 ml of dry N,N-dimethylformamide, 335 mg (1 mmol) of N-(2-methoxy-3,4-methylenedioxybenzyl)-p-toluenesulfonamide (1) and 0.18 ml (1.1 mmol) of bromoacetaldehyde diethylacetal (purity 95%) were added in order. The resulting mixture was stirred at 100° C. for 10 hours. On cooling, to this 5 ml of water was added and the reaction mixture was extracted with 8 ml and then 2 ml of methylene chloride successively. The liquid extract was washed with 5 ml of water, dried over anhydrous magnesium sulfate and filtered. The filtrate was concentrated under vacuum and the residue was purified by silica gel column chromatography (eluate: ethylacetate/n-hexane=¼) to obtain 358 mg of N-(2-methoxy-3,4-methylenedioxybenzyl)-N-(p-toluenesulfonyl)aminoacetaldehyde diethylacetal (2) as an oil. Yield 79%.

REFERENCE EXAMPLE 6

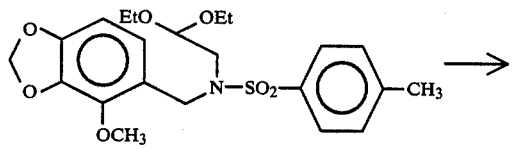

(1)

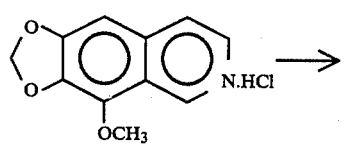

(2)

-continued

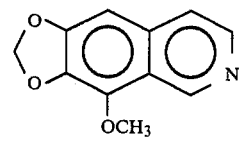

(3)

69.89 g (0.155 mol) of N-(2-methoxy-3,4-methylenedioxybenzyl)-N-(p-toluene sulfonyl) aminoacetaldehyde diethylacetal (1) obtained in Example 13 was dissolved in 194 ml of dioxane, to which 14.7 ml (0.169 mol) of concentrated hydrochloric acid and 47.1 ml of water were added. The resulting mixture was heated under reflux for two hours and 40 minutes and cooled to about 5° C. The deposited crystals were collected by filtration and washed with 30 ml of cold dioxane and then dried to obtain 22.95 g of 8-methoxy-6,7-methylenedioxyisoquinoline hydrochloride (2) as a yellow crystal (yield 61.8%).

17.8 g (74.3 mmol) of the compound (2) thus obtained was added to 50 ml of water, to which 100 ml of methylene chloride was added. This solution was made basic with 25% aqueous solution of sodium hydroxide under water-cooling. The solution was separated and the aqueous layer was extracted with 20 ml of methylene chloride. The obtained methylene chloride layers were combined, washed with 30 ml of water, dried over anhydrous magnesium sulfate and then concentrated under vacuum to obtain 15.06 g of 8-methoxy-6,7-methylenedioxyisoquinoline (3) (yield 99.7%). The product thus obtained was recrystallized from ethylacetate-n-hexane, m.p. 144°-5° C. IR and NMR spectra of the resultant product are listed below.

IR(KBr, $\nu$max cm$^{-1}$): 1595, 1460, 1040
$^1$H—NMR(60 MHz in CDCl$_3$, $\delta$ppm):

4.17 (3H, s, OC$\underline{H}_3$)

5.97 (2H, s, C$\underline{H}_2$⟨O—/O—⟩)

6.72 (1H, s, 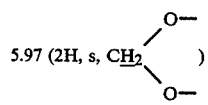)

7.35 (1H, d, J=6Hz, 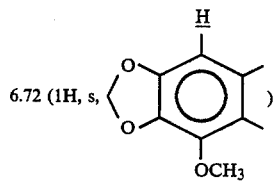)

8.30 (1H, d, J=6Hz, 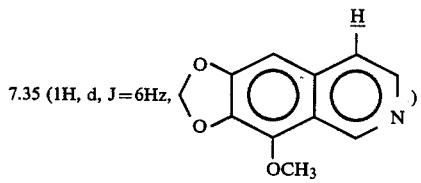)

9.30 (1H, s, 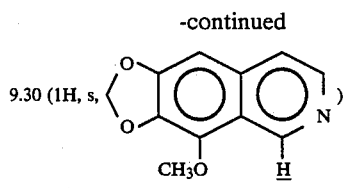)

6.27 (1H, s, 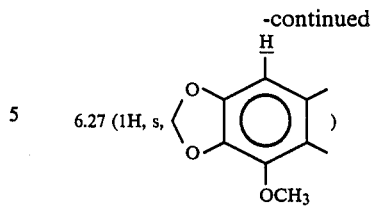)

REFERENCE EXAMPLE 7

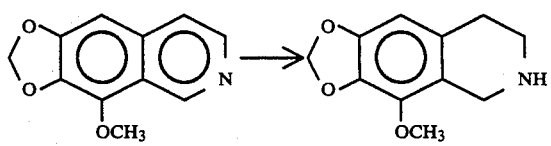

(1)          (2)

0.5 g of platinum oxide catalyst was added to 20 ml of acetic acid, through which hydrogen was passed for 30 minutes with stirring. Then, 4.06 g (20 mmol) of 8-methoxy-6,7-methylenedioxyisoquinoline (1) obtained in Reference Example 6 was added to carry out catalytic reduction at 75° C. at atmospheric pressure for 17 hours. On cooling, the catalyst was filtered out and the filtrate was concentrated under vacuum. 20 ml of water and 20 ml of methylene chloride were added to the residual oil, which was made basic by 25% aqueous solution of sodium hydroxide under ice-cooling. The solution was separated and the aqueous layer was extracted with 5 ml of methylene chloride. The obtained methylene chloride layers were combined, washed with 10 ml of water, dried over anhydrous magnesium sulfate and then concentrated under vacuum. The resultant residue was purified by silica gel column chromatography (eluate: methanol/chloroform=1/20 and then ⅓) to obtain 3.23 g of 8-methoxy-6,7-methylene-dioxy-1,2,3,4-tetrahydroisoquinoline (2) as a crystal. Yield 78%. NMR spectra of the resultant product are listed below.

<u>¹H—NMR(60 MHz in CDCl₃, δppm):</u>
2.44   (1H, s, N<u>H</u>)

2.79   (2H, t, J=5Hz)
3.18   (2H, t, J=5Hz)   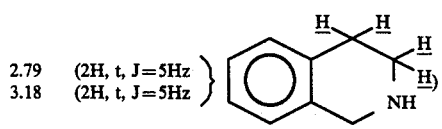

3.87 (2H, s, 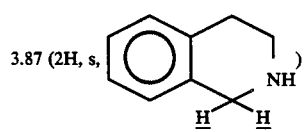)

3.97 (3H, s, OC<u>H</u>₃)

5.82   (2H, s, C<u>H</u>₂ 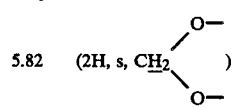)

REFERENCE EXAMPLE 8

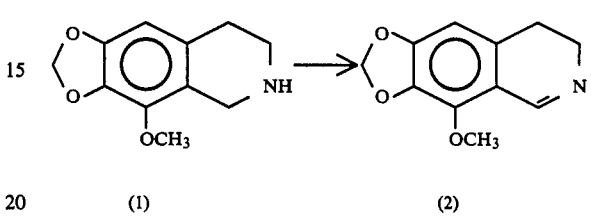

(1)          (2)

2.07 g (10 mmol) of 8-methoxy-6,7-methylenedioxy-1,2,3,4-tetrahydroisoquinoline (1) obtained in Reference Example 7 was dissolved into 20 ml of methanol, to which 8.94 g (12 mmol) of 10% aqueous solution of sodium hypochlorite was added little by little under ice-cooling. The resulting mixture was stirred at room temperature for one hour and 40 minutes, 1.5 g (35.6 mmol) of 95% sodium hydroxide was added to the reaction mixture, which was then refluxed for one hour. 10 ml of water was added and most of methanol was distilled off under vacuum. The aqueous layer was extracted with 15 ml and then 10 ml of toluene successively. After washing the liquid extract with 10 ml of water, it was dried over anhydrous magnesium sulfate and the solvent was distilled off under vacuum to obtain 2.00 g of 8-methoxy-6,7-methylenedioxy-3,4-dihydroisoquinoline (2). Yield 97%.

REFERENCE EXAMPLE 9

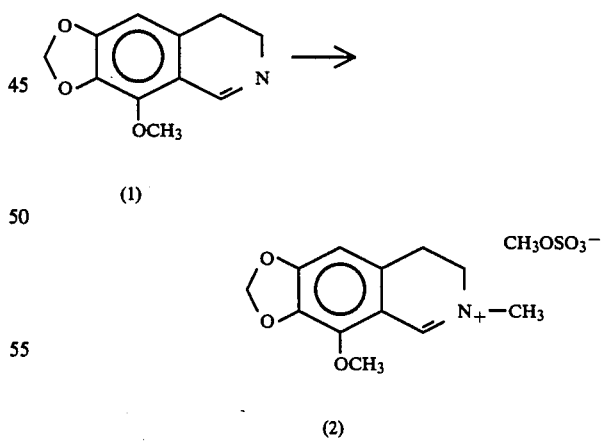

1.96 g (9.55 mmol) of 8-methoxy-6,7-methylenedioxy-3,4-dihydroisoquinoline (1) obtained in Example 8 was dissolved into 30 ml of toluene, to which 1.08 ml (11.5 mmol) of dimethylsulfate was added. The resulting mixture was left for over night. The deposited crystals were filtered out washed with toluene and then dried to obtain 3.05 g of 8-methoxy-2-methyl-6,7-methylenedioxy-3,4-dihydroisoquinolinium methyl sulfate (2). Yield 96%.

REFERENCE EXAMPLE 10

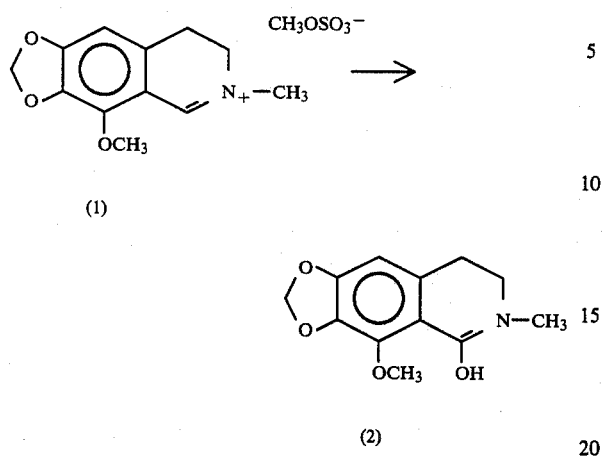

1.657 g (5 mmol) of 8-methoxy-2-methyl-6,7-methylenedioxy-3,4-dihydroisoquinolinium methyl sulfate (1) obtained in Reference Example 9 was dissolved in 20 ml of water, to which 3 ml of 25% aqueous solution of sodium hydroxide was added at a temperature lower than 20° C. The resulting mixture was stirred at room temperature for 30 minutes, the deposited crystals were collected by filtration, washed with each 3 ml of water twice and dried under vacuum to obtain 964 mg of cotarnine (2). Yield 81%.

EXAMPLE 14

Preparation of N-methyl-2-methoxy-3,4-methylenedioxybenzylamine 5.0 g of 2-methoxy-3,4-methylenedioxybenzaldehyde was suspended in 30 ml of methanol, to which 4.31 g of 40% methylamine aqueous solution (2 equivalent) was added. 59 mg of 5% Pd/C catalyst (0.1 mol %) was added to the obtained reaction mixture and hydrogenation was carried out at ordinary temperature and atmospheric pressure. Absorption of hydrogen was completed in about 2 hours to quantitatively obtain N-methylbenzylamine derivative. The catalyst was filtered out and excessive methylamine, water formed and methanol solvent were distilled off to obtain an oily N-methyl-2-methoxy-3,4-methylenedioxybenzylamine. (Yield 100%).

EXAMPLE 15

Preparation of N-(2-methoxy-3,4-methylenedioxybenzyl)-N-methylaminoacetaldehyde dimethyl acetal 0.98 g of N-methyl-(2-methoxy-3,4-methylenedioxybenzylamine obtained in Example 14, 0.93 g (1.1 equivalent) of bromoacetaldehyde dimethylacetal and 0.76 g (1.5 equivalent) of triethylamine as base were mixed in 7.3 ml of toluene and heated under reflux for 4 hours. On cooling the reaction mixture to room temperature, the deposited salts were filtered out and the toluene layer was analyzed to show that 1.302 g of the desired N-(2-methoxy-3,4-methylenedioxybenzyl)-N-methylaminoacetaldehyde dimethylacetal was obtained. Yield 92%. Because 0.25 g of excessive triethylamine was present in the toluene layer, a toluene solution of the desired N-(2-methoxy-3,4-methylenedioxybenzyl)-N-methylaminoacetaldehyde dimethylacetal was obtained by distilling off excessive triethylamine at atmospheric pressure.

EXAMPLE 16

32.5 g of 2-methoxy-3,4-methylenedioxy-N-methylbenzylamine, 12.8 g of sodium hydroxide, 38.4 g of water and 29.72 g (1.1 equivalent) of bromoacetaldehyde dimethylacetal were collectively charged in 65 ml of toluene and stirred under heating in an oil bath at 100° C. for 8 hours. On cooling the reaction mixture to room temperature, the toluene layer was separated, washed with water and analyzed to show that 47.2 g of the desired N-(2-methoxy-3,4-methylenedioxybenzyl)-N-methylaminoacetaldehyde dimethylacetal only was present in the toluene layer. Yield 100%. No other organic compound was present therein.

EXAMPLES 17–20

The reactions were carried out in the same manner as in Example 16 except for modifying the conditions as shown in Table 1. The results are shown in Table 1.

TABLE 1

| Example No. | (II) Equivalent/(I) | NaOH Equivalent/(I) | H₂O ml/g(I) | Temperature °C. (bath temp.) | Time hr | (I) Conversion rate % | (III) Yield % | (III) Selectivity % |
|---|---|---|---|---|---|---|---|---|
| 17 | 1.05 | 9.3 | 5 | 120 | 5 | ~100 | 100 | 100 |
| 18 | 1.10 | 4.9 | 5 | 120 | 5 | ~100 | 98 | 98 |
| 19 | 1.10 | 2.0 | 5 | 120 | 5 | ~100 | 96 | 96 |
| 20 | 1.10 | 1.2 | 5 | 120 | 5 | ~100 | 98 | 98 |

COMPARATIVE EXAMPLE

When the reaction was carried out in the same manner as in Example 16 except for not adding alkali (NaOH), the yield of the desired product was 30%.

EXAMPLE 21

To 100 ml of ethanol, were charged 1.83 ml of ethanol containing 22.2 g of hydrochloric acid dissolved therein, 3.96 g of N-methylaminoacetaldehyde dimethylacetal, 1.0 g of 2-methoxy-3,4-methylenedioxybenzaldehyde, 0.35 g of sodium cyanoborohydride and 10 ml of ethanol, and they were stirred in an oil bath under a nitrogen stream at 70° C. for 2 hours. After the reaction was over, the reaction mixture was cooled to room temperature, made alkaline (pH 11) with 2N NaOH solution and extracted with ethyl acetate. The liquid extract was analyzed by GC and LC to show, as a product, 1.50 g of 2-methoxy-3,4-methylenedioxy-N-methylbenzylamino dimethylacetal (yield 95%) and 0.046 g of 2-methoxy-3,4-methylenedioxy benzylalcohol (yield 4.9%), while 2-methoxy-3,4-methylenedioxy benzaldehyde of the starting material not being recognized (conversion rate:100%). The selectivity to the desired 2-methoxy-3,4-methylenedioxy-N-methylbenzylamino dimethylacetal was 95%.

EXAMPLE 22

To 100 ml of ethanol, were charged 1.83 ml of ethanol containing 22.2 g of hydrochloric acid dissolved therein, 3.96 g of N-methylaminoacetaldehyde dimethylacetal, 1.0 g of 2-methoxy-3,4-methylenedioxybenzaldehyde, 10 ml of ethanol and 0.12 g of 5% palladium on carbon catalyst, and hydrogenation was carried out at room temperature for 3.5 hours. The amount of hydrogen absorption was 120% of the theoretical amount. After the reaction was over, the catalyst was filtered out and 2N NaOH aqueous solution was added to the reaction mixture to make the filtrate alkaline (pH 11). The resulting mixture was then extracted with ethyl acetate. The liquid extract was analyzed by GC and LC to show 1.47 g of 2-methoxy-3,4-methylenedioxy-N-methylbenzylamino dimethylacetal (yield 93%), 0.012 g of 2-methoxy-3,4-methylenedioxybenzylalcohol (yield 1%) and 7.4 mg of 2-methoxy-3,4-methylenedioxy toluene (yield 0.8%), while 2-methoxy-3,4-methylenedioxybenzaldehyde of the starting material not being recognized. The selectivity to the desired 2-methoxy-3,4-methylenedioxy-N-methylbenzylamino dimethylacetal was 99%.

EXAMPLE 23

To 100 ml of ethanol, were charged 0.9 ml of ethanol containing 22.2 g of hydrochloric acid dissolved therein, 1.98 g of N-methylaminoacetaldehyde dimethylacetal, 1.0 g of 2-methoxy-3,4-methylenedioxybenzaldehyde, 10 ml of ethanol and 0.12 g of 5% palladium on carbon catalyst and hydrogenation was carried out at room temperature. The reaction was completed in 3 hours. The amount of hydrogen absorption was 103% of the theoretical amount. After the reaction was over, the catalyst was filtered out and 2N NaOH aqueous solution was added to the reaction mixture to make the filtrate alkaline (pH 11). The resulting mixture was then extracted with ethyl acetate. The liquid extract was analyzed by GC and LC to show 1.29 g of 2-methoxy-3,4-methylenedioxy-N-methylbenzylamino dimethylacetal (yield 82%), 0.11 g of 2-methoxy-3,4-methylenedioxybenzylalcohol (yield 11%) and 0.02 mg of 2-methoxy-3,4-methylenedioxy toluene (yield 2%), while 2-methoxy-3,4-methylenedioxybenzaldehyde of the starting material not being recognized (conversion rate:100%). The selectivity to the desired 2-methoxy-3,4-methylenedioxy-N-methylbenzylamino dimethylacetal was 88%.

EXAMPLE 24

The reaction was carried out in the same manner in Example 23 except for using 0.22 g of 5% platinum on carbon catalyst. The amount of hydrogen absorption was 111% of the theoretical amount. After the reaction was over, the catalyst was filtered out and 2N NaOH aqueous solution was added to the reaction mixture to make the filtrate alkaline (pH 11). The resulting mixture was then extracted with ethyl acetate. The liquid extract was analyzed by GC and LC to show 1.32 g of 2-methoxy-3,4-methylenedioxy-N-methylbenzylamino dimethylacetal (yield 84%), 0.13 g of 2-methoxy-3,4-methylenedioxybenzyl alcohol (yield 13%) and 4 mg of 2-methoxy-3,4-methylenedioxy toluene (yield 0.4%), and 0.6 mg of 2-methoxy-3,4-methylenedioxybenzaldehyde of the starting material (conversion rate:100%). The selectivity to the desired 2-methoxy-3,4-methylenedioxy-N-methylbenzylamino dimethylacetal was 87%.

EXAMPLE 25

To 100 ml of methanol, were charged 0.16 ml of methanol containing 25 g of hydrochloric acid dissolved therein, 0.79 g of N-methylaminoacetaldehyde dimethylacetal, 1.0 g of 2-methoxy-3,4-methylenedioxybenzaldehyde, 0.35 g of sodium cyanoborohydride and 10 ml of ethanol and stirred in an oil bath under a nitrogen stream at 70° C. for 2 hours. After the reaction was over, the reaction mixture was cooled to room temperature and 2N NaOH aqueous solution was added thereto to make the filtrate alkaline (pH 11). The resulting mixture was then extracted with ethyl acetate. The liquid extract was analyzed by GC and LC to show, as a product, 0.88 g of 2-methoxy-3,4-methylenedioxy-N-methylbenzylamino dimethylacetal (yield 56%) and 0.44 g of 2-methoxy-3,4-methylenedioxybenzyl alcohol (yield 44%), while 2-methoxy-3,4-methylenedioxybenzaldehyde of the starting material being not recognized (conversion rate:10%). The selectivity to the desired 2-methoxy-3,4-methylenedioxy-N-methylbenzylamino dimethylacetal was 56%.

EXAMPLE 26

To 100 ml of ethanol, were charged 0.18 ml of ethanol containing 22.2 g of hydrochloric acid dissolved therein, 0.79 g of N-methylaminoacetaldehyde dimethylacetal, 1.0 g of 2-methoxy-3,4-methylenedioxybenzaldehyde, 0.12 g of 5% palladium on carbon catalyst and 10 ml of ethanol, and hydrogenation was carried out in an oil bath at 70° C. for 2 hours. The amount of hydrogen absorption was 100% of the theoretical amount. After the reaction was over, the catalyst was filtered out and 2N NaOH aqueous solution was added to the reaction mixture to make the filtrate alkaline (pH 11). The resulting mixture was then extracted with ethyl acetate. The liquid extract was analyzed by GC and LC to show 1.32 g of 2-methoxy-3,4-methylenedioxy-N-methylbenzylamino dimethylacetal (yield 84%), 0.02 g of 2-methoxy-3,4-methylene-dioxybenzylalcohol (yield 2%), 0.076 g of 2-methoxy-3,4-methylenedioxytoluene (yield 8%) and 0.007 g of 2-methoxy-3,4-methylenedioxybenzaldehyde of the starting material (conversion rate:99%). The selectivity to the desired 2-methoxy-3,4-methylenedioxy-N-methylbenzylamino dimethylacetal was 98%.

What is claimed is:
1. A benzylamine derivative of the formula I:

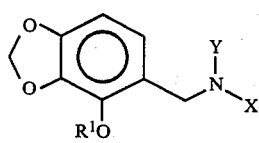
(I)

wherein R¹ represents a hydrogen atom or a methyl group, X represents a hydrogen atom, a methyl group or a tosyl group, and Y represents

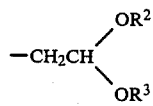

in which R² and R³ being identical or different from each other represent independently a lower alkyl group.

2. The benzylamine derivative as defined in claim 1 wherein R¹ represents a hydrogen atom, X represents a hydrogen atom or a methyl group and Y represents

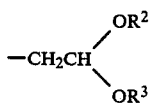

in which R² and R³ are as defined in claim 1.

3. The benzylamine derivative as defined in claim 1 wherein R¹ represents a methyl group, X represents a hydrogen atom, a methyl group or a tosyl group and Y represents

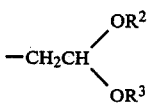

in which R² and R³ are as defined in claim 1.

4. The benzylalmine derivative as defined in claim 1 wherein R¹ represents a methyl group, X represents a hydrogen atom or a methyl group and Y represents,

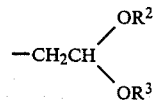

in which R² and R³ are as defined in claim 1.

5. An N-methylbenzylaminoacetal derivative of formula II:

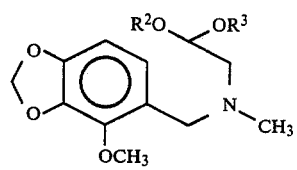
(II)

wherein R² and R³ each represent a lower alkyl group.

6. The N-methylbenzylaminoacetal derivative as defined in claim 5 in which R² and R³ each represent a lower alkyl group of 1 to 5 carbon atoms.

7. The N-methylbenzylaminoacetal derivative as defined in claim 6 in which R² and R³ each represent a lower alkyl group of 1 to 3 carbon atoms.

8. A benzylamine derivative of the formula:

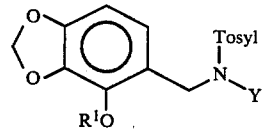

wherein R¹ and Y are each hydrogen or methyl.

9. The benzylamine derivative of claim 8, wherein R¹ is methyl and Y is hydrogen.

10. A benzylamine derivative of the formula:

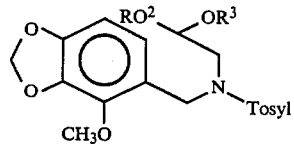

where R² and R³ independently each are a lower alkyl group.

* * * * *